United States Patent
Rheinheimer et al.

(10) Patent No.: US 6,824,985 B1
(45) Date of Patent: *Nov. 30, 2004

(54) FORMULATION FOR REDUCING UREA EFFECT FOR IMMUNOCHROMATOGRAPHY ASSAYS USING URINE SAMPLES

(75) Inventors: Gary W. Rheinheimer, Goshen, IN (US); Meitak Teresa Yip, Elkhart, IN (US)

(73) Assignee: Bayer Corporation, Elkhart, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 908 days.

(21) Appl. No.: 08/925,998

(22) Filed: Sep. 9, 1997

(51) Int. Cl.[7] .............................................. G01N 33/53
(52) U.S. Cl. ...................... 435/7.1; 435/7.92; 435/7.93; 435/7.94; 435/7.95; 435/962; 435/970; 435/5; 435/27; 436/514; 436/518; 436/525; 436/810; 436/825
(58) Field of Search ................................ 435/7.1, 7.92, 435/7.93, 7.94, 7.95, 962, 970, 5, 27; 436/514, 518, 525, 810, 825

(56) References Cited

U.S. PATENT DOCUMENTS

| | | | | |
|---|---|---|---|---|
| 4,065,445 A | * | 12/1977 | Bohn et al. ................... 530/394 |
| 4,362,531 A | * | 12/1982 | de Steenwinkel et al. .. 436/512 |
| 4,446,232 A | * | 5/1984 | Liotta ........................... 436/514 |
| 4,604,348 A | * | 8/1986 | Neurath ....................... 435/7.92 |
| 4,619,896 A | * | 10/1986 | Shattock et al. ................. 435/5 |
| 4,690,801 A | * | 9/1987 | Anderson ..................... 422/61 |
| 4,725,556 A | * | 2/1988 | Mareschal et al. ........... 436/500 |
| 4,729,875 A | * | 3/1988 | Chandler ....................... 422/58 |
| 4,861,711 A | * | 8/1989 | Friesen et al. .............. 435/7.92 |
| 5,081,013 A | * | 1/1992 | Rovelli et al. .............. 435/7.92 |
| 5,120,643 A | * | 6/1992 | Ching et al. ................ 435/7.92 |
| 5,264,348 A | * | 11/1993 | Schick et al. .................. 435/28 |
| 5,294,369 A | * | 3/1994 | Shigekawa et al. .......... 436/525 |
| 5,350,855 A | * | 9/1994 | Daniloff et al. ............. 546/291 |
| 5,369,013 A | * | 11/1994 | Citri ............................. 435/27 |
| 5,502,197 A | * | 3/1996 | Daniloff et al. ........... 546/278.7 |
| 5,723,619 A | * | 3/1998 | Hatch .......................... 546/250 |
| 5,744,096 A | * | 4/1998 | Jones et al. .................. 422/58 |
| 5,750,411 A | * | 5/1998 | Sommer ..................... 436/525 |
| 5,756,679 A | * | 5/1998 | Daniloff et al. ............. 530/363 |
| 5,834,610 A | * | 11/1998 | Johnson ...................... 546/300 |
| 5,858,645 A | * | 1/1999 | Kuzuya et al. |
| 6,214,541 B1 | * | 4/2001 | Zentgraf et al. ................ 435/5 |

FOREIGN PATENT DOCUMENTS

EP 638 806 * 2/1995 .................. 435/7.1

OTHER PUBLICATIONS

N. Tietz, ed., "Textbook of Clinical Chemistry" published by W.B. Saunders Company Philadelphia, pp. 1848–1849, 1986.*

* cited by examiner

Primary Examiner—L. F. Smith
Assistant Examiner—Ginny Allen Portner

(57) ABSTRACT

Disclosed is an improvement in the analysis for an analyte in a urine test sample in which the urine is contacted with a labeled antibody specific to the analyte and the concentration of the analyte is determined by measuring the response from the label. The improvement involves maintaining the concentration of urea in the test sample above the threshold value which value is the concentration of urea at which increases in the urea concentration do not affect the accuracy of the assay such as by interfering with the binding between the analyte and the labeled antibody.

10 Claims, 4 Drawing Sheets

FORMULATION FOR REDUCING UREA EFFECT FOR IMMUNOCHROMATOGRAPHY ASSAYS USING URINE SAMPLES

BACKGROUND OF THE INVENTION

There exists a need for simple diagnostic tests for common diseases which can be carried out by untrained personnel. Such tests facilitate home or doctor's office testing as opposed to more complicated procedures which require that the analysis be carried out in an outside reference laboratory. A common format for these tests involves the use of an immunostrip. Typically, this format involves a matrix of a material through which a fluid test sample, such as urine, can flow by capillarity. The matrix, typically in the form of a strip through which the test fluid flows horizontally, contains an antibody specific for the analyte whose presence and/or concentration is being sought which antibody bears a detectable label, so that the presence and/or concentration of the analyte in the test fluid can be determined by detection of the signal emitted from the detectable label. A classical embodiment of such a device, sometimes referred to as an immunochromatographic strip, is illustrated by FIG. 1. Referring to FIG. 1, strip 10 bears a labeled antibody, specific for the analyte under investigation, in zone 13 which binds with the analyte in the fluid test sample applied to the wicking zone 12 of the strip 10 which may contain a buffer and flows along the strip to form an immunocomplex which further migrates due to capillary action through the capture zone of the strip 14 and the optional detection zone 16. In the capture zone 14 there is immobilized the analyte or a derivative thereof which is immunoreactive with the antibody and is able to capture labeled antibody which has not reacted with analyte in the fluid test sample. The signal from the labeled antibody captured in the capture zone is measured and related to the concentration of analyte in the test fluid in an inverse relationship since the greater the concentration of analyte in the test sample, the amount of labeled antibody which is unbound and thereby free to specifically bind with the analyte immobilized in the capture zone is diminished. Detection zone 16 is optional but can contain immobilized anti-mouse IgG to bind the analyte/labeled binding partner complex and thereby serve as a means for verifying that the test has been carried out correctly.

Urine is a common test fluid for this sort of assay, and it has now been discovered that urea, whose concentration in urine will vary tends to interfere with the binding between the antibody and analyte in the system. The degree of such interference will vary depending on the particular antibody and antigen involved in the assay. Urea is synthesized in the liver as the final product of amino acid catabolism. Urea excretion is proportionate to protein intake and dependent on the protein metabolism, it increases with a high protein diet. Normal adults excrete about 20.6 g of urea per day. The interferences with the antigen/antibody binding tend to cause the assay to have a negative bias when the urine test sample contains more than the normal amount of urea. It would be desirable, and it is an object of the present invention to provide a method and a device which reduce or eliminate the bias caused by the fluctuations in urea concentration in urine.

SUMMARY OF THE INVENTION

The present invention is a method for the analysis of an analyte in a urine test sample in which a labeled antibody specific to the analyte is combined with the urine and the concentration of analyte in the urine is determined by the magnitude of the response from the labeled antibody which is a function of the amount of binding of the labeled antibody with the analyte. According to the present invention, the assay is improved upon by maintaining the concentration of urea in the urine above a threshold value which is the concentration at which increases in urea do not affect the binding between the analyte and the labeled antibody. Also included within the scope of the present invention is a test device for carrying out the improved assay.

DESCRIPTION OF THE INVENTION

Figure 1:
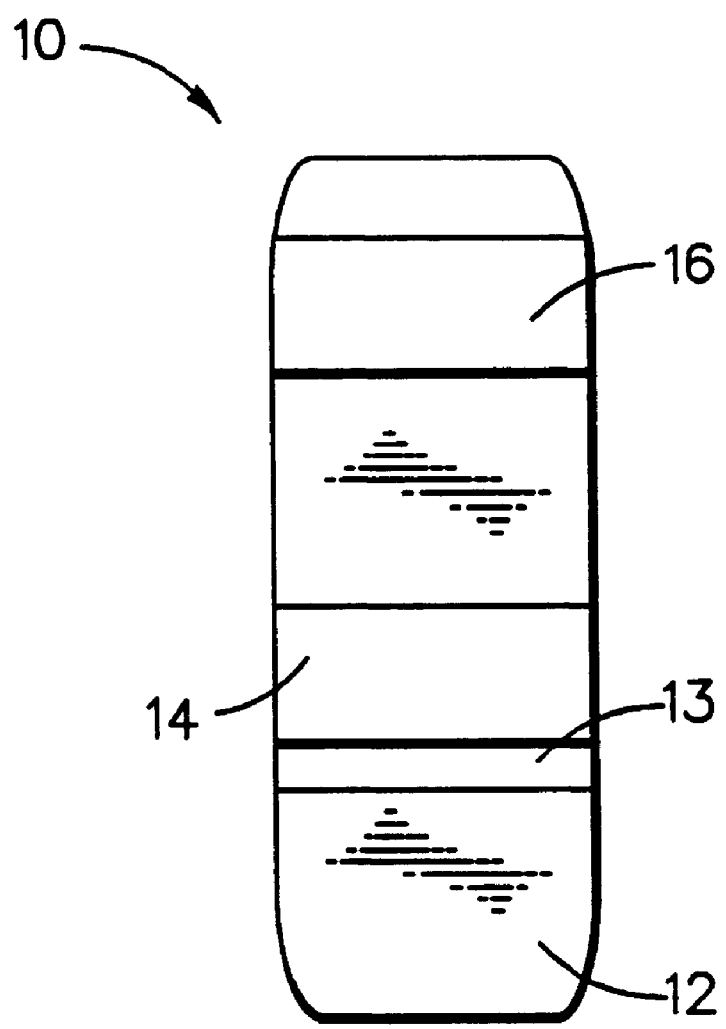
FIG. 1 represents a type of test strip which is suitable for use in carrying out the present invention.

While the assay improvement of the present invention can be carried out in a wet system such as a microtitre plate assay, it is typically employed in conjunction with an immunostrip format. In this format, the invention is practiced by first providing a test strip in the form of a matrix through which the test sample together with analyte contained therein and the labeled antibodies can flow by capillarity. Typically, the matrix will be in the form of a strip through which the test fluid flows horizontally, although the matrix could be set up in layers through which the test fluid would flow vertically from top to bottom or vice-versa. The following discussion focuses on the strip format. The strip can be prepared from any material through which the urine test sample, analyte and labeled antibody can flow by capillarity. Accordingly, suitable matrix materials include nitrocellulose, polysulfones, polycarboxylic acids, and filter paper.

A particularly suitable immunochromatographic strip format for use in relation with the present invention is that which is disclosed in U.S. Pat. No. 4,446,232 wherein there is described a device for the determination of the presence of antigens which comprises a strip of a matrix material having a first zone in which there are provided enzyme linked antibodies specific to the analyte to be determined and a second zone containing immobilized analyte. Upon application of the fluid test sample, the labeled antibodies can flow through the second zone when reacted with analyte introduced along with the test fluid but will not so flow in the absence of analyte in the test fluid due to their being bound in this zone by interaction with the immobilized analyte. The analyte is typically an antigen although the format can be designed to detect the presence of antibodies as analyte. An alternative to this format is that in which the capture zone contains an immobilized binding partner which is specific for an epitope of the analyte different than that to which the labeled antibody is specific. This format provides a means for capturing the labeled binding partner using the so-called sandwich format. In another modification, there is disposed in a separate region of the strip an immobilized binding partner for the conjugate such as anti-mouse IgG to thereby capture the complex formed between the labeled specific binding partner and the analyte. Thus, by immobilizing the conjugate in a discrete detection zone located downstream on the strip from the zone in which the labeled binding partner for the analyte is bound, there are provided two zones from which the physically detectable property of the detectable label can be measured to determine its intensity and hence the concentration of the detectable label in a particular region of the strip. By measuring the signal from the physically detectable label in the zone containing the immobilized analyte or binding partner specific to a defined epitope of the analyte as the capture means and the physically detectable property of the label in the detection zone, and determining the ratio of these signals, the accuracy of the test for analyte concentration can be increased.

Regardless of the selection of the format for the assay, the accuracy of the final result can be skewed by changes of the urea concentration in the urine test sample caused by normal fluctuation in the urine's urea concentration and it is the goal of the present invention to reduce or eliminate this bias. This is accomplished by maintaining the concentration of urea in the urine test sample above a threshold value which is the concentration of urea at which increases in its concentration do not further affect the binding between the analyte and the labeled antibody.

Figure 2:
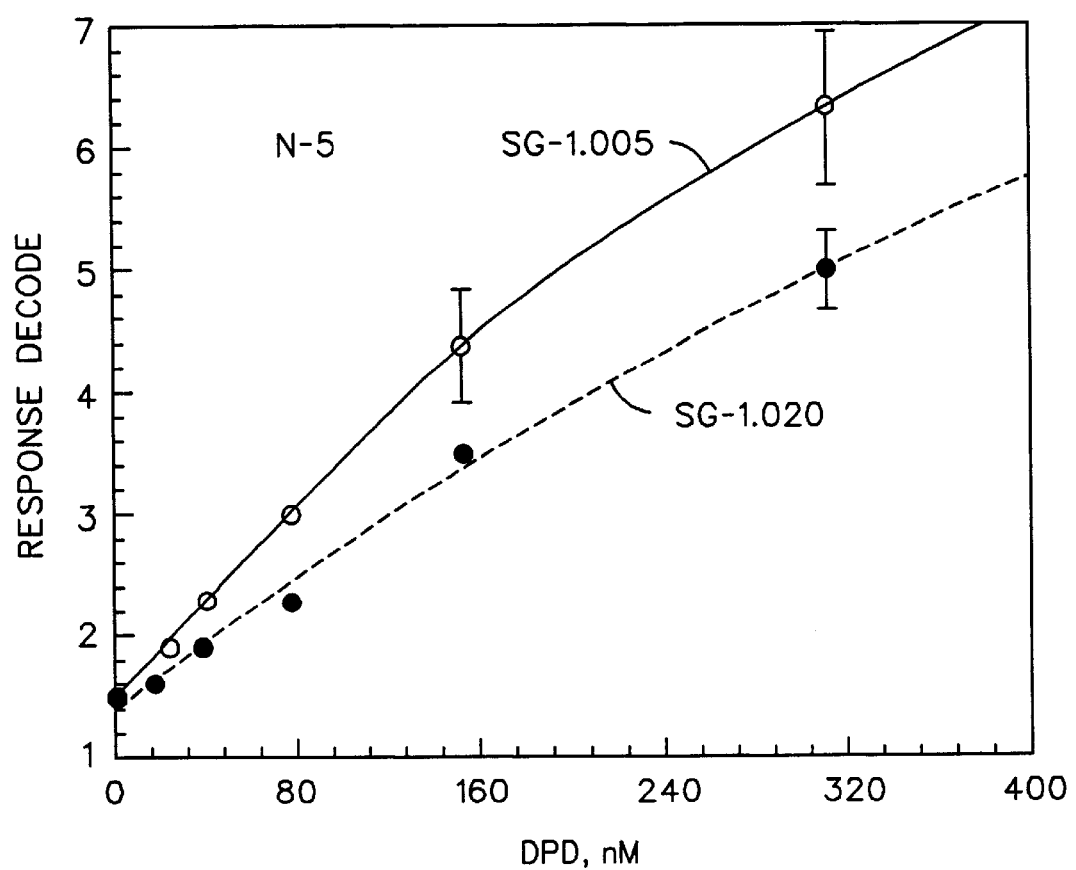
FIG. 2 graphically illustrates the bias introduced to an analysis of urine by raising the urine's specific gravity.
Figure 3:
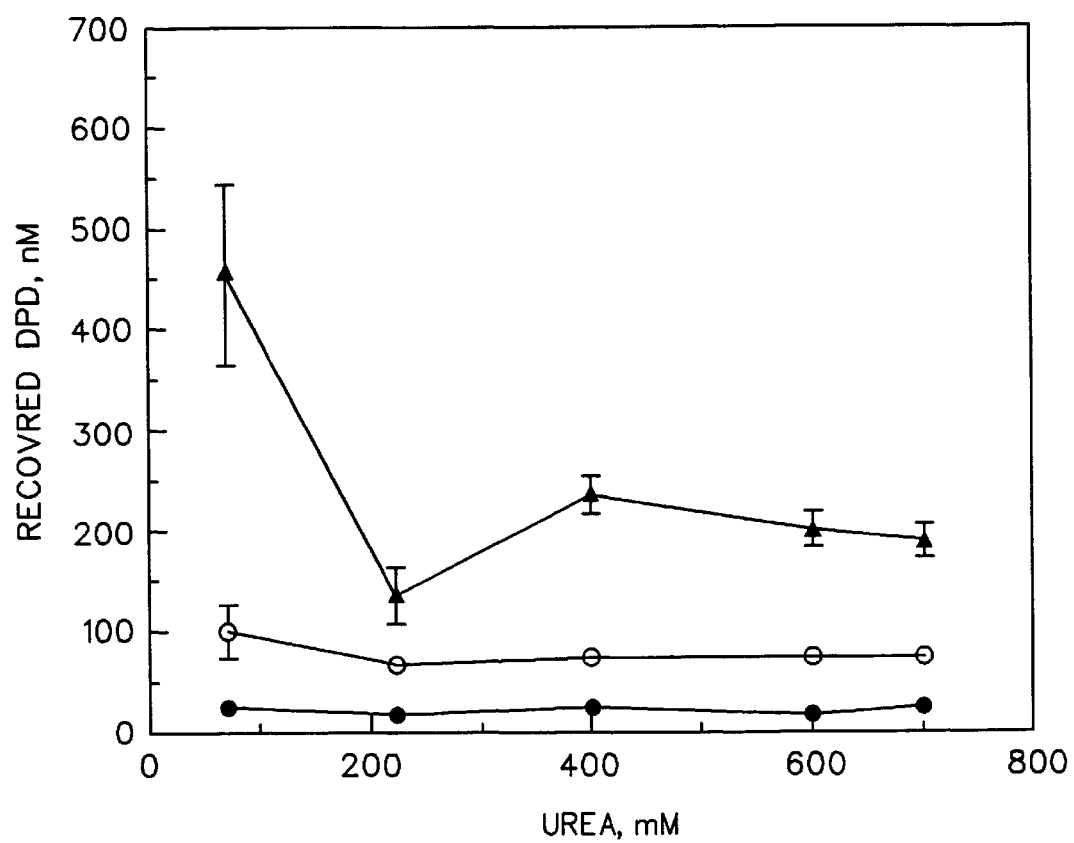
FIG. 3 graphically illustrates the plateau of the urea interference in urine assays when the urea concentration reaches 225 mM.

In an assay for deoxypyridinoline (DPD), a known bone resorption marker, in which a gold sol labeled anti-DPD antibody was reacted with immobilized DPD it was found that bias was introduced by changes in specific gravity, and that high specific gravity resulted in a negative bias of 33%. This is graphically illustrated by FIG. 2 in which high specific gravity (SG=1.020) gave lower apparent DPD concentrations than were obtained with low specific gravity (SG=1.005) urine. This led to the hypothesis that the bias could be the result of urea interference with the labeled antibody-antigen binding. Another experiment was performed using DPD as the analyte, in which three levels of DPD test solutions were prepared containing different concentrations of urea. The three levels of DPD were 25, 75 and 250 nM and the urea concentrations were 75, 225, 400, 600 and 700 nM. The recovered DPD concentrations of these solutions were obtained from the standard curve generated using calibrators containing 400 mM of urea. The results shown in FIG. 3 indicate that the urea interference reaches a plateau at urea concentrations of greater than 225 mM. Thus, by providing an assay for DPD in which the urea concentration is maintained at a level of at least 225 mM, the bias caused by urea will remain steady and can be compensated for by using calibrators containing similar concentrations of urea. The urea concentration at which analytes other than DPD exhibit the plateau effect may be lower or higher than 225 mM, but can be readily determined for each analyte by routine experimentation such as that which is described herein for DPD. Accordingly, based on this discovery, which is the essence of the present invention, it is possible to factor out of the assay results bias caused by urea interference with antigen-labeled antibody binding in immunologic urinalysis. This is accomplished by combining at least the threshold level of urea with the urine test sample before it is contacted with the labeled antibody. In a liquid state assay, the necessary amount of urea can be combined with the urine sample or to the microtitre plate in which the labeled antibodies are disposed. In the case of an immunochromatographic strip format, the urea can be added to the strip's wicking pad or to a separate buffer pad included as an integral part of the strip. This is accomplished by impregnating the strip's pad with an aqueous solution of urea followed by drying, so that the urea will be made available by rehydration upon contacting the strip with the urine sample. Any of these methods will provide the necessary urea concentration. It is, however, preferred to combine the urea with the buffer pad to provide a unitary device which will automatically introduce the desired urea concentration to the urine sample upon contacting it with the strip. It is preferred to incorporate the urea into the buffer pad because it is in this area that the urine test sample first contacts the test device and combining the buffer and urea is the most efficient method for introducing the additional urea to the urine sample.

Many clinically significant analytes are present in urine which are determinable by means of the present invention. Among these analytes are deoxypyridinoline (DPD), human albumin, drugs of abuse, cancer markers, and human choronic gonatropin (hCG). The detectable label for the analyte may be any moiety which is detectable by reproducible means. Thus, the label can be an enzyme, a radioisotope, a chemilluscent material or a visible particulate label such as gold sol or latex particles.

The present invention is further illustrated by the following example.

EXAMPLE I

Three formulations of buffer-urea pads, 4" (10.2 cm)×17.7"(45 cm) of Whatman F075-07 membrane were prepared by hand impregnation. One formulation contained 1 M glycine for buffer at pH 8.6 and 300 mM urea. The second contained 1 M glycine at pH 8.6 and 400 mM urea. The third was used as a control and contained only 1 M glycine at pH 8.6. After impregnation, the buffer-urea pads were dried in a convection drier for 30 minutes at 40° C. The pad was then slit into 0.5"×17.7" strips.

The capture reagent was DPD-PEG, a poly(ethylene glycol) derivatized DPD, in 0.05 mg/mL concentration. The detection reagent was goat anti-mouse IgG in 0.3 mg/mL concentration. The striping of capture and detection reagents was done with an IVEK linear striper on Millipore nitrocellulose, 1" (2.54 cm)×17.7" (45 cm).

The gold sol-anti-DPD pad was prepared by impregnation of a 4" (10.2 cm)×17.7" (45 cm) strip of Whatman F075-07 membrane with gold sol-anti-DPD suspension (OD at 530 nm=1.7). OD is optical density which is a measure of concentration of gold sol-anti-DPD in the suspension. The pad was then slit into 0.25"×17.7" strips.

The above pads were assembled together onto a polystyrene backing material, 4" (10.2 cm)×17.7" (45 cm), according to the configuration shown in FIG. 1 by lamination and then slit into test strips of 4" (10.2 cm)×0.2" (5 mm).

The strips were developed by dipping them in aqueous solutions containing 0, 20, 40, 80, 160 and 320 mMolar concentrations of DPD and either 75 mM or 600 mM of urea. The dose response decode was determined using the green filter on a CLINITEK 50® reflectance spectrometer.

Figure 4:
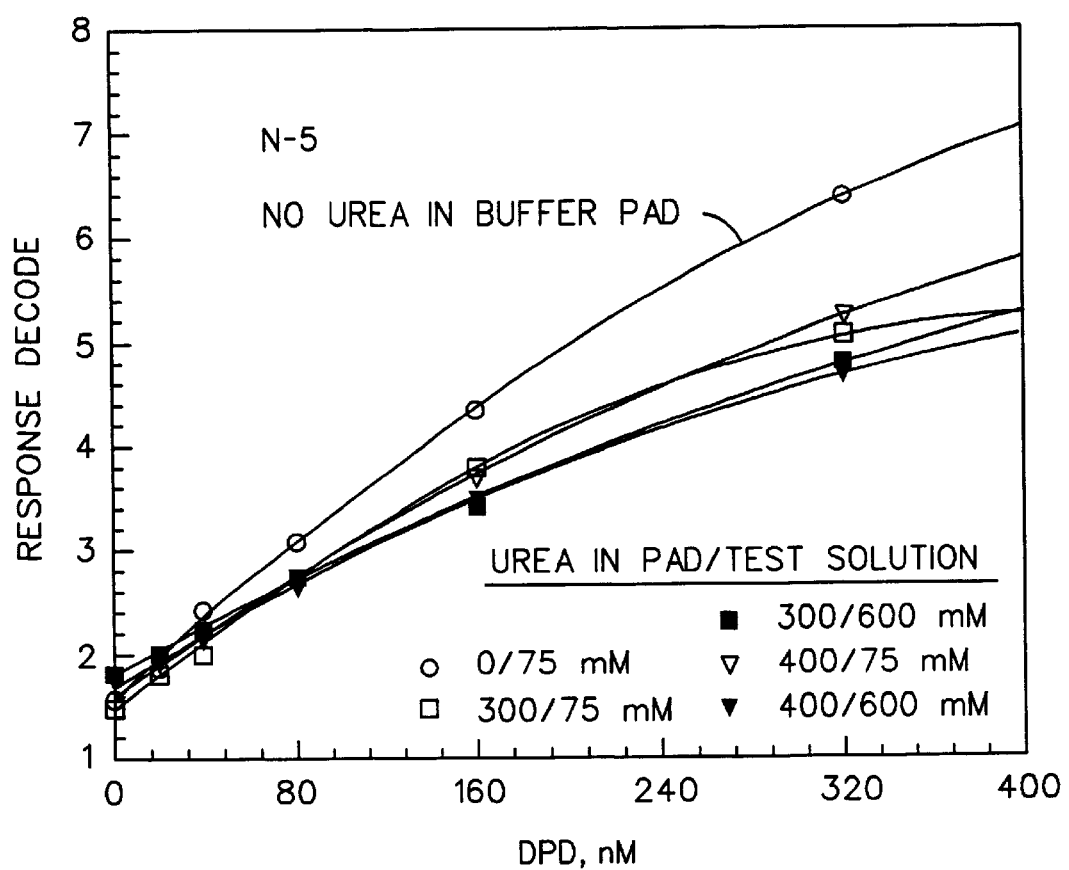
FIG. 4 illustrates the discovery that the addition of urea to an assay of urine can limit the bias caused by the urea effect.

The results of this experiment are graphically represented by FIG. 4. As can be determined from FIG. 4, those strips with 300 mM or 600 mM urea incorporated into the buffer pad gave dose response results which were grouped together for test solutions containing either 75 or 600 mM urea. Conversely, the results obtained using the strip with no urea in the buffer pad are significantly different from the others. With the total urea concentration (0+75 mM=75 mM) much less than the threshold value of 225 mM, the responses of the immunoactivity are higher than those with total urea concentrations of 375, 900, 475 and 1000 mM. Also, the results indicate that for the four conditions where the total urea concentrations are higher than 225 mM, their dose response curves are very similar. These data demonstrate the favorable effect that urea addition to the test sample has in offsetting result variance caused by fluctuations of urea in the urine.

What is claimed is:

1. In an analysis for an analyte in a urine test sample in which antibodies having a detectable label and which are specific to the analyte are combined with the urine test sample and the concentration of the analyte in the urine test sample is determined by the amount of binding of the antibodies having the detectable label with the analyte by measuring the magnitude of the response from the detectable label and comparing the magnitude of the response from the detectable label with responses obtained from calibrators containing similar amounts of urea, the improvement which comprises determining a threshold of urea concentration in the urine test sample which level is greater than that normally found in urine and at which increases in the urea concentration do not affect the accuracy of the analysis and maintaining the concentration of urea in the urine test sample above the threshold value by adding urea thereto.

2. The analysis of claim 1 which is carried out in a matrix of an absorbant material through which the urine test sample, the analyte and the labeled antibody flow by capillarity.

3. The analysis of claim 2 wherein the matrix of absorbent material is nitrocellulose, a polysulfone, a polycarboxylic acid or filter paper.

4. The analysis of claim 1 wherein the analyte is deoxypyridinoline and sufficient urea is combined with the urine test sample to provide a urea concentration therein of greater than 225 mM.

5. The analysis of claim 1 carried out in a microtiter plate.

6. The analysis of claim 1 wherein the analysis carried out in a matrix of an absorbant material in the form of a strip wherein the labeled antibodies are stored in a distinct portion of the strip and which strip has a buffer containing pad upstream from the labeled antibodies in which the urea necessary to increase the concentration of urea in the urine test sample is stored.

7. A test strip for the determination of an analyte in a urine test sample which test strip comprises a matrix of an absorbent material through which the urine test sample, the analyte and antibodies which bear a detectable label can flow by capillarity and which strip has a region containing mobile antibodies bearing a detectable label and which are specific for the analyte and, upstream from the labeled antibody containing region, a region containing dry urea in sufficient quantity so that when the urea is rehydrated upon contact with the urine test sample when the urine test sample is applied to the strip there will be provided a concentration of urea in the urine test sample which is above the level normally found in urine and which has been determined to be above a threshold value at which increases in the urea concentration do not affect binding between the analyte and the antibodies bearing the detectable label.

8. The test strip of claim 7 in which the region containing the antibodies bearing the detectable label also contains a buffer.

9. The test strip of claim 8 wherein the antibodies are specific to deoxypyridinoline and the concentration of urea in the dry urea containing region of the strip is sufficient to raise the concentration of urea in the urine test sample to greater than 225 mM upon application of the urine test sample to the strip and rehydration of the dry urea by the so applied urine test sample.

10. An assay for deoxypyridinoline in urine which comprises applying a urine test sample to a test strip of nitrocellulose which strip has a region containing gold sol labeled antibodies specific for deoxypyridinoline and upstream from the gold sol labeled antibody containing region there is a region containing dry urea in sufficient concentration to raise the level of urea in the urine test sample when it is rehydrated upon contact with the urine test sample to a level of greater than 225 mM.

\* \* \* \* \*